US00PP17531P2

(12) United States Plant Patent
Wülfinghoff

(10) Patent No.: US PP17,531 P2
(45) Date of Patent: Mar. 27, 2007

(54) ***ALSTROEMERIA* PLANT NAMED 'LUCCA'**

(50) Latin Name: *Alstroemeria hybrida*
Varietal Denomination: Lucca

(76) Inventor: Hermann Joseph Paul Wülfinghoff, P.O. Box 34, 2280 AA, Rijswijk (NL)

( * ) Notice: Subject to any disclaimer, the term of this patent is extended or adjusted under 35 U.S.C. 154(b) by 18 days.

(21) Appl. No.: 11/178,013

(22) Filed: Jul. 8, 2005

(51) Int. Cl.
*A01H 5/00* (2006.01)

(52) U.S. Cl. ..... Plt./309

(58) Field of Classification Search ..... Plt./309
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Alstroemeria* plant named 'Lucca', characterized by its upright and strong flowering stems; durable and long-lasting leaves; freely flowering habit; light red and yellow-colored flowers; and good post-production longevity.

1 Drawing Sheet

Botanical designation: *Alstroemeria hybrida.*
Cultivar denomination: 'Lucca'.

BACKGROUND OF THE INVENTION

The present Invention relates to a new and distinct cultivar of *Alstroemeria* plant, botanically known as *Alstroemeria hybrida*, commercially used as a cut flower *Alstroemeria*, and hereinafter referred to by the name 'Lucca'.

The new *Alstroemeria* is a product of a planned breeding program conducted by the Inventor in Wateringen, The Netherlands. The objective of the breeding program was to develop new cut flower *Alstroemeria* cultivars with freely flowering habit, large flowers, attractive flower colors and excellent postproduction longevity.

The new *Alstroemeria* originated from a cross-pollination made by the Inventor in Wateringen, The Netherlands, in 1999 of a selection of *Alstroemeria hybrida* identified as code number 201, not patented, as the female, or seed, parent with a selection of *Alstroemeria hybrida* identified as code number 140, not patented, as the male, or pollen, parent. The new *Alstroemeria* was discovered and selected by the Inventor as a flowering plant within the progeny of the stated cross-pollination in a controlled environment in Wateringen, The Netherlands in 1999.

Asexual reproduction of the new cultivar by tissue culture in a controlled environment in Wateringen, The Netherlands, has shown that the unique features of this new *Alstroemeria* are stable and reproduced true to type in successive generations of asexual propagation.

SUMMARY OF THE INVENTION

Plants of the cultivar Lucca have not been observed under all possible environmental conditions. The phenotype may vary somewhat with variations in environment such as temperature and light intensity without, however, any variance in genotype.

The following traits have been repeatedly observed and are determined to be the unique characteristics of 'Lucca'. These characteristics in combination distinguish 'Lucca' as a new and distinct cultivar:

1. Upright and strong flowering stems.
2. Durable and long-lasting leaves.
3. Freely flowering habit.
4. Light red and yellow-colored flowers.
5. Good postproduction longevity.

Plants of the new *Alstroemeria* can be compared to plants of the parent selections. Plants of the new *Alstroemeria* have more durable leaves and larger flowers than plants of the parent selections.

Plants of the new *Alstroemeria* can also be compared to plants of the cultivar Orange Favorite, not patented. In side-by-side comparisons conducted in Geldern, Germany, plants of the new *Alstroemeria* differed from plants of the cultivar Orange Favorite in the following characteristics:

1. Plants of the new *Alstroemeria* had shorter flowering stems than plants of the cultivar Orange Favorite.
2. Plants of the new *Alstroemeria* produced more flowering stems per year than plants of the cultivar Orange Favorite.
3. Plants of the new *Alstroemeria* were more freely flowering than plants of the cultivar Orange Favorite.
4. Plants of the new *Alstroemeria* had larger flowers than plants of the cultivar Orange Favorite.
5. Plants of the new *Alstroemeria* and the cultivar Orange Favorite differed in flower color as plants of the cultivar Orange Favorite had orange-colored flowers.

BRIEF DESCRIPTION OF THE PHOTOGRAPHS

The accompanying colored photographs illustrate the overall appearance of the new *Alstroemeria*, showing the colors as true as it is reasonably possible to obtain in colored reproductions of this type. Colors in the photographs may differ slightly from the color values cited in the detailed botanical description which accurately describe the colors of the new *Alstroemeria.*

The photograph at the top of the sheet comprises a side perspective view of a typical flowering stem of 'Lucca' grown in a container.

The photograph at the bottom of the sheet is a close-up view of a typical flower of 'Lucca'.

DETAILED BOTANICAL DESCRIPTION

The aforementioned photographs, following observations and measurements describe plants of the new *Alstroemeria* grown during the spring in ground beds in Geldern, Germany in a glass-covered greenhouse for about three months. During the production of the plants, day temperatures were about 11° C. and night temperatures were about 7° C. Color references are made to The Royal Horticultural Society Colour Chart, 2001 Edition, except where general terms of ordinary dictionary significance are used.

Botanical classification: *Alstroemeria hybrida* cultivar Lucca.

Parentage:

*Female parent.*—*Alstroemeria hybrida* selection identified as code number 201, not patented.

*Male parent.*—*Alstroemeria hybrida* selection identified as code number 140, not patented.

Propagation:

*Type.*—By tissue culture.

*Root description.*—Fibrous, fleshy, thick; white, close to 155D, in color.

*Rooting habit.*—Freely branching.

*Rhizomes.*—Shape: Elongate; rounded. Length: About 5 cm. Diameter: About 1.2 cm. Texture: Smooth. Color: 155C.

Plant description:

*Plant habit.*—Upright and strong flowering stems; freely basal branching, bushy appearance. Vigorous growth habit.

*Plant height.*—About 180 cm.

*Plant diameter* (*spread*).—About 80 cm.

*Number of harvestable flowering stems per year.*—About 80 to 100 per plant.

*Flowering stem description.*—Aspect: Upright. Length: About 180 cm. Internode length: About 3 to 7 cm. Strength: Strong. Texture: Glabrous, smooth. Color: 137B.

*Foliage description.*—Length, largest: About 17 cm. Width, largest: About 3.5 cm. Shape: Lanceolate. Apex: Acute. Base: Attenuate. Margin: Entire. Texture, upper and lower surfaces: Smooth, glabrous. Venation pattern: Parallel. Durability: Durable, long-lasting. Petiole length: About 3 cm. Petiole diameter: About 5 mm. Petiole texture, upper and lower surfaces: Smooth, glabrous. Color: Developing foliage, upper surface: 136B. Developing foliage, lower surface: 135B. Fully expanded foliage, upper surface: 137A. Fully expanded foliage, lower surface: 137B. Venation, upper and lower surfaces: 138B. Petiole, upper surface: Close to 137A. Petiole, lower surface: Close to 137B.

Flower description:

*Flower type and habit.*—Single cup-shaped flowers arranged in compound umbels. Flowers face mostly outward. Perianth segments separate. Freely and continuously flowering. Flowers not persistent.

*Natural flowering season.*—Flowering continuous year-round under greenhouse conditions.

*Fragrance.*—None detected.

*Flower longevity on the plant.*—About one to three weeks.

*Flower longevity as a cut flower.*—About seven to ten days.

*Flower buds* (*showing color*).—Length: About 6.5 cm. Diameter: About 2 cm. Shape: Ovoid. Color: 40A; towards the apex, 142A; venation, 179A.

*Umbel height.*—About 18 cm.

*Umbel diameter.*—About 23 cm.

*Number of flowers per umbel.*—About three to nine.

*Flower diameter.*—About 7 cm.

*Flower height.*—About 6 cm.

*Perianth.*—Arrangement: Six arranged in two whorls, each whorl with two lateral and one median segments. Size, inner perianth segments: Length, lateral segments: About 6 cm. Length, median segment: About 5.1 cm. Width, lateral segments: About 2 cm. Width, median segment: About 2 cm. Size, outer perianth segments: Length, lateral segments: About 6.4 cm. Length, median segment: About 6.4 cm. Width, lateral segments: About 3.5 cm. Width, median segment: About 3.5 cm. Shape, inner perianth, all segments: Lanceolate. Shape, outer perinath, all segments: Rounded. Apex, inner perianth, all segments: Acute; mucronate. Apex, outer perianth, all segments: Bracket-shaped; mucronate. Base, inner and outer perianths, all segments: Attenuate. Margin, inner and outer perianths, all segments: Entire. Texture, inner and outer perianths, all segments: Smooth, glabrous. Color, inner perianth: When opening and fully opened, lateral segments, upper surface: 44B; center section, 22A; spots, close to 59A. When opening and fully opened, median segment, upper surface: 44B; spots, close to 59A. When opening and fully opened, lateral and median segments, lower surface: 44B. Color, outer perianth: When opening and fully opened, lateral and median segments, upper surface: 44B. When opening and fully opened, lateral and median segments, lower surface: 44B.

*Pedicels.*—Length: About 6 cm. Diameter: About 3 mm. Strength: Strong. Angle: About 40° to 45° from vertical. Texture: Smooth, glabrous. Color: 138A and 139A.

*Reproductive organs.*—Stamens: Quantity per flower: Six. Anther shape: Oval. Anther length: About 9 mm. Anther diameter: About 2 mm. Anther color: 167A. Pollen amount: Abundant. Pollen color: 164A. Pistils: Quantity per flower: One. Pistil length: About 5 cm. Style length: About 4.5 cm. Style color: 43C. Stigma color: 39B. Ovary color: 144A.

*Fruits.*—Shape: Globular. Length: About 6 mm. Diameter: About 6 mm. Color: 144A.

*Seeds.*—Seed development has not been observed.

Disease/pest resistance: Plants of the new *Alstroemeria* have not been observed to be resistant to pathogens and pests common to *Alstroemerias*.

Temperature tolerance: Plants of the new *Alstroemeria* have been observed to tolerate temperatures from 0 to 40° C.

It is claimed:

1. A new and distinct cultivar of *Alstroemeria* plant named 'Lucca', as illustrated and described.

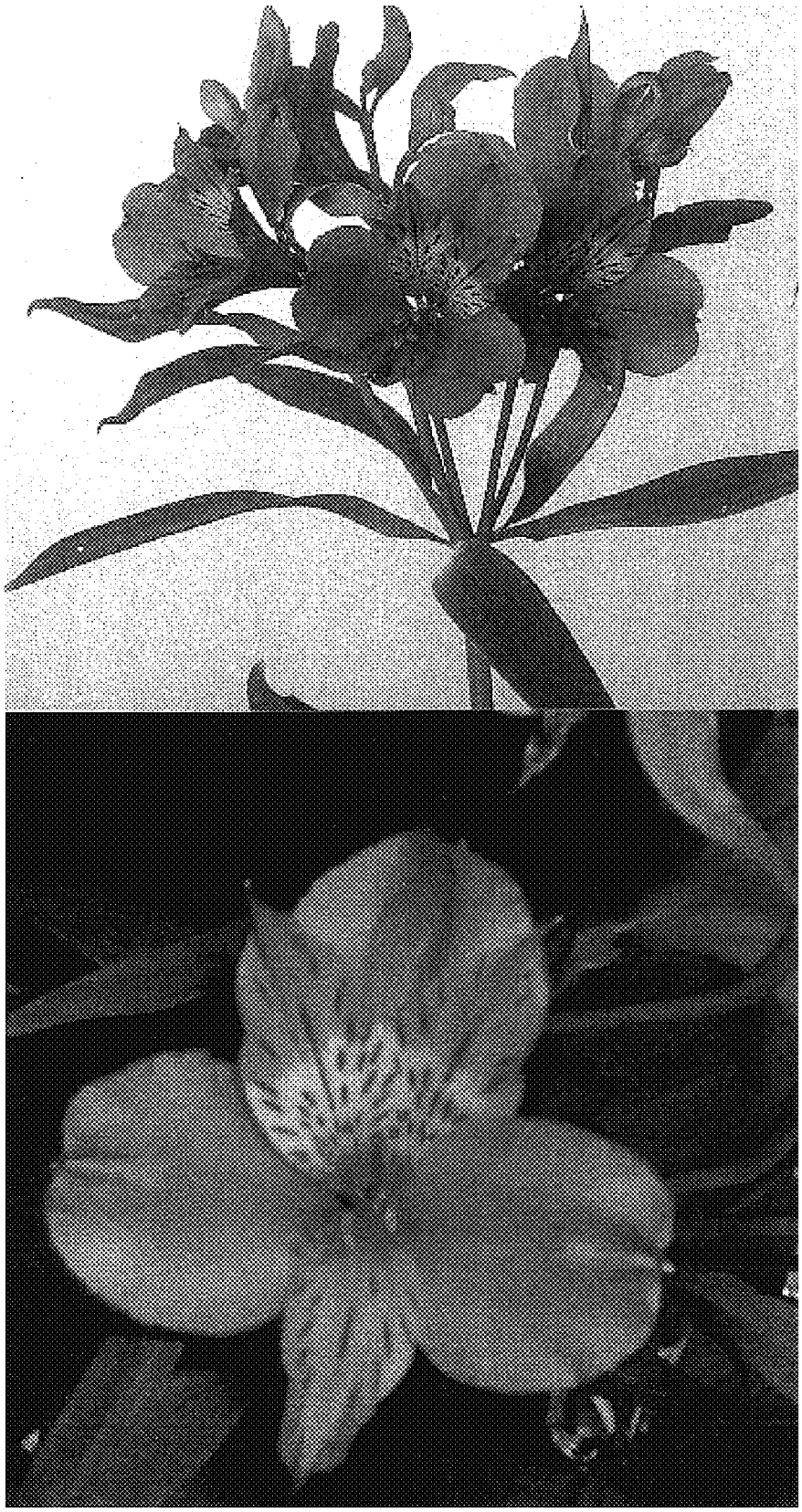

* * * * *